US005476488A

United States Patent [19]
Morgan et al.

[11] Patent Number: 5,476,488
[45] Date of Patent: Dec. 19, 1995

[54] TELEMETRY SYSTEM POWER CONTROL FOR IMPLANTABLE MEDICAL DEVICES

[75] Inventors: Wayne A. Morgan, Granada Hills; Tom W. Richards, San Luis Obispo, both of Calif.

[73] Assignee: Pacesetter, Inc., Sylmar, Calif.

[21] Appl. No.: 168,734

[22] Filed: Dec. 15, 1993

[51] Int. Cl.$^6$ .................................................. A61N 1/00
[52] U.S. Cl. ............................... 607/30; 128/903; 607/32; 340/870.05
[58] Field of Search ................................ 607/30, 32, 60; 128/903; 340/870.05, 870.31, 825.54

[56] References Cited

U.S. PATENT DOCUMENTS

| | | | |
|---|---|---|---|
| 4,223,679 | 9/1980 | Schulman et al. | 128/419 PT |
| 4,681,111 | 7/1987 | Silvian | 128/419 PT |
| 4,741,341 | 5/1988 | Marach | 128/419 PT |
| 4,847,617 | 7/1989 | Silvian | 340/870.16 |
| 4,944,299 | 7/1990 | Silvian | 128/419 PG |
| 5,058,581 | 10/1991 | Silvian | 128/419 PG |
| 5,107,833 | 4/1992 | Barsness | 128/903 |
| 5,117,825 | 6/1992 | Grevious | 607/32 |
| 5,324,315 | 6/1994 | Grevious | 128/903 |
| 5,325,046 | 6/1994 | Young et al. | 340/870.31 |

*Primary Examiner*—William E. Kamm
*Assistant Examiner*—Marianne Parker
*Attorney, Agent, or Firm*—Harold C. Schloss

[57] ABSTRACT

During the telemetering of telemetry signals between an implantable medical device and an external programmer, the transmitter power of the implantable device is dynamically adjusted. The programmer measures the strength of the telemetry signals transmitted by the implantable device. A power control signal is generated as a function of the measured signal strength, and the transmitter power of the implantable device is set to a power level specified by the power control signal. For example, if the measured signal strength falls below a predetermined minimum signal strength threshold, power must be increased. This process is repeated until the measured signal strength satisfies a predetermined signal strength condition.

33 Claims, 5 Drawing Sheets

TELEMETRY SYSTEM POWER CONTROL FOR IMPLANTABLE MEDICAL DEVICES

FIELD OF THE INVENTION

The present invention relates to telemetry systems for implantable medical devices and, more particularly, to the control of transmitter power in such devices.

BACKGROUND OF THE INVENTION

The surgical implantation of electronic devices in humans and animals has become a commonplace occurrence. These implantable medical devices perform either observational or regulatory functions. Observational functions include the monitoring of certain body functions, such as heart rate. Regulatory functions may take the form of electrical stimulation to body tissue, nerves or organs. The cardiac pacemaker is perhaps the most commonly known implantable medical device, and is an example of one that performs both observational and regulatory functions. The pacemaker or "pacer" monitors the heart to determine whether it is beating properly, and, if not, the pacer stimulates the heart muscle to restore a regular heartbeat.

In order for an implantable device to perform its functions at minimum inconvenience and risk to the person or animal within whom it is used, such devices perform noninvasive bidirectional telemetry to allow data and commands to be passed back and forth between the implantable device and an external transceiver. The transceiver, known by a variety of names, such as controller, programmer or monitor, receives the data from the implantable device. The data may take the form of device identification information, biological data, or battery charge condition, among others. Based upon this data, the programmer can transmit commands to the implantable device to optimize performance.

A number of techniques have been used for communicating noninvasively with an implantable device. The system shown in U.S. Pat. No. 4,223,679, issued to Schulman et al., and assigned to the assignee of the present invention, illustrates one example. That telemetry system transmits information from an implanted medical device to an external programmer by relying on the reflected impedance of an internal inductive circuit in the implanted device. The internal inductive circuit is energized by an inductively coupled external inductive circuit that is located in the programmer. The implanted device modulates the internal inductive circuit using frequency shift keying. By measuring the reflected impedance of the internal inductive circuit, the external programmer receives information transmitted from the implanted device. Because the energy used to transmit the information is provided by the programmer through the external inductive circuit, the implanted device uses little or no current to perform telemetry. Unfortunately, this system has speed limitations making it unsuitable for transmitting the amount of information currently required by medical telemetry systems.

Another type of device uses an active transmitter; that is, the transmitted energy is provided by the implantable device battery rather than from external sources. Such a device is illustrated in U.S. Pat. No. 4,944,299, issued to Silvian, and assigned to the assignee of the present invention. The techniques used in active systems have achieved higher data transmission rates than those used in passive devices.

By their nature, active transmitters require more power from the implantable device than passive transmitters. The power consumed by an implantable device is one of the most, if not the most, important factor in designing such devices. Implanted systems are customarily powered by a long-lasting non-replaceable internal battery. For example, the life of a pacemaker battery averages approximately five to seven years. During normal operation, conventional pacemakers experience a current drain on the order of tens of micro amperes ($\mu A$). Conventional telemetry systems can drain up to fifteen additional $\mu A$ from the pacer battery. When the battery voltage decreases below a prescribed amount, the entire pacer must be surgically replaced.

One other design consideration is that the information conveyed between an implanted medical device and an external programmer must be accurate and nearly error-free because of the risks to the human or animal in whom the device is implanted. During the design of the device, it is programmed to transmit a predetermined digital signal. The signal is received outside the device and compared to the predetermined transmitted signal. A measure of signal quality known as the bit error rate (BER) is then calculated according to the following formula: BER =(number of bits in the received signal that are not identical to the bits in the same bit positions in the transmitted signal)/(total number of bits in the signal). The major factors in determining this signal quality measurement include ambient electrical noise and the distance between the device and the programmer. Accurate telemetry requires a bit error rate on the order of $10^4$.

To ensure satisfactory telemetry during normal operation after implantation, the device transmitter is designed with enough radiated power to guarantee an acceptable error rate under worst case conditions. Conventional systems assume telemetry in an electrically noisy environment at a maximum distance of approximately four inches, and set the transmitter power level of the implantable device accordingly to maintain effective telemetry under those conditions. Typically, this level is fixed and not adjustable after the pacemaker has been implanted. However, in many circumstances after implantation, telemetry is carried out in relatively quiet environments at less than the maximum telemetry distance. Thus, the worst case is not frequently realized. Although telemetry is guaranteed under this scenario, setting power according to worst case assumptions causes unnecessary power consumption and a shortening of potential battery life.

SUMMARY OF THE INVENTION

The present invention overcomes the drawbacks and limitations of the conventional telemetry systems that are discussed above. The present invention guarantees satisfactory telemetry, while at the same time minimizing the power consumption of an implantable medical device. This objective is achieved by dynamically adjusting the transmitter power of the implantable device after it has been implanted.

In accordance with the present invention, a programmer external to the implantable device continually monitors the signal strength of a telemetry signal received from the implantable device. The signal strength may be represented by several measurements, including the voltage level of the received signal measured at the programmer, and the signal-to-noise ratio, among others. The programmer compares the received signal strength with either a minimum signal strength threshold alone or with both the minimum threshold and a maximum signal strength threshold. The minimum threshold represents the minimum acceptable signal strength and corresponds to an acceptable bit error rate. The maximum signal strength threshold indicates that transmitter power is causing an unacceptable current drain on the device battery.

In one embodiment, the programmer uses both thresholds and determines whether the received signal strength is greater than the minimum signal strength threshold and less than the maximum signal strength threshold. If the signal quality is within those bounds, then the transmitter power need not be adjusted. However, if the signal strength is less than the minimum threshold, then the programmer transmits a power adjustment signal to the implantable device instructing it to increase its transmitter power to ensure satisfactory telemetry. On the other hand, if the received signal strength is greater than the maximum threshold, then the programmer transmits a signal to the implantable device instructing it to decrease its transmitter power to avoid unnecessary current drain on the implantable device battery.

Alternatively, the present invention may use only the minimum threshold. Telemetry is initiated at a maximum transmitter power level. The programmer measures the received signal strength and compares it to the minimum threshold. If the received signal strength is greater than the threshold, the programmer instructs the implantable device to decrease its transmitter power. The power may be decreased in fixed steps, or adjusted according to a binary search tree, among other algorithms. The programmer will continue to request decreased power until the measured signal strength falls below the minimum threshold. At that time, the programmer will instruct the implantable device to increase its transmitter power. After requesting the increase, the programmer will continue to monitor the received signal strength, but will prevent any further adjustment of transmitter power until the signal strength again falls below the minimum threshold, if ever. By providing this condition, the present invention prevents the received signal strength from hovering around the minimum threshold point. This avoids continual adjustment of the transmitter power, until adjustment is necessary to guarantee adequate telemetry.

In a further embodiment, the programmer includes an automatic gain control. In that case, the signal strength may be measured using the gain of the AGC. The AGC gain is inversely proportional to the signal-to-noise ratio, signal voltage level and similar signal strength measurements, i.e., a high gain setting represents a low level signal while a low AGC gain setting indicates a strong signal. Thus, the roles of the thresholds discussed above must be reversed to achieve proper operation of the present invention using an AGC.

In further embodiments, the power adjustment signal sent by the programmer to the implantable device may represent two alternative quantities. The signal may simply indicate that power is to be increased or decreased as a result of the comparison of the received signal strength to the threshold(s). In response, the implantable device calculates its transmitter power setting from this signal. This embodiment may be denoted the "smart device" mode. Alternatively, the power adjustment signal does not simply represent the change to be made to the transmitter power, but the actual power setting itself that is used by the implantable device. This manner of power setting is denoted the "smart programmer" mode.

The system of the present invention thereby allows the transmitter power of an implantable medical device to be adjusted dynamically after it has been implanted. The present invention adjusts transmitter power to maintain satisfactory telemetry in the environment in which it is operating, while at the same time minimizing the current drain on the implantable device battery. Thus, transmitter power may be adjusted to meet real world conditions, which may not necessarily be the same as the worst case conditions used in the laboratory to fix the power of conventional implantable device transmitters. These advantages make the system of the present invention a highly desirable improvement over the current state of the art.

BRIEF DESCRIPTION OF THE DRAWINGS

The objects, features and advantages of the present invention will be apparent to one skilled in the art in light of the following detailed description in which.

DETAILED DESCRIPTION OF THE INVENTION

The present invention provides a method and apparatus for telemetry system power control for an implantable medical device. The present invention will be described in the context of a telemetry system including a pacemaker and a corresponding programmer. Of course, the present invention is applicable to telemetry involving any implantable device. Moreover, for purposes of explanation, specific embodiments are set forth to provide a thorough understanding of the present invention. However, it will be apparent to one skilled in the art that the invention may be practiced without these details. In other instances, well known elements, devices, process steps and the like are not set forth in detail in order to avoid unnecessarily obscuring the present invention.

Figure 1:
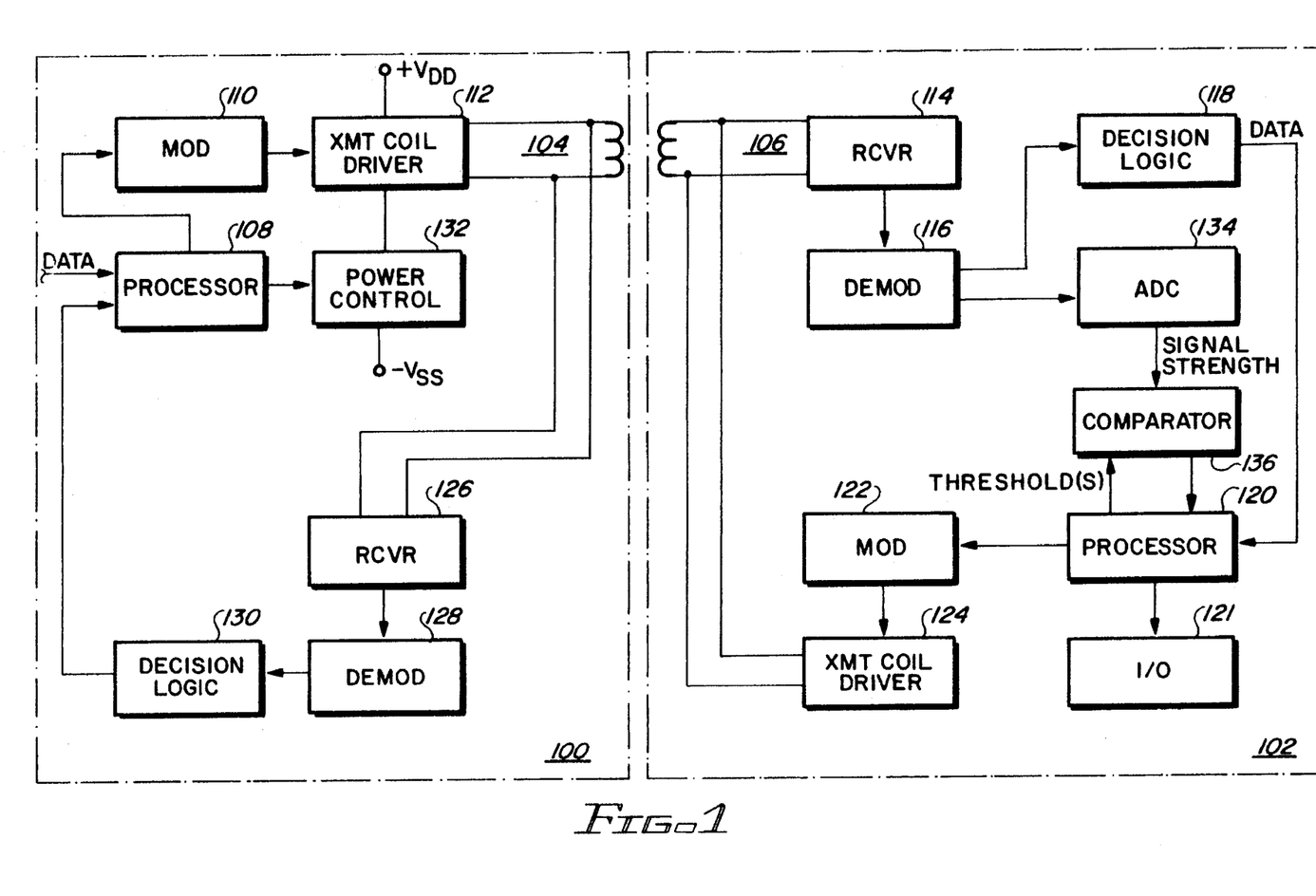
FIG. 1 illustrates an embodiment of the telemetry system of the present invention.

FIG. 1 illustrates an embodiment of the telemetry system of the present invention. A pacemaker 100 communicates with a programmer 102 through inductive coupling between a pacemaker coil 104 and a programmer coil 106. When operating as a conventional pacer, the pacemaker 100 transmits data to the programmer 102 and receives commands from the programmer 102. The data may, for example, represent digitized electrocardiogram (ECG) signals from a heart (not shown). The data is initially fed into a processor 108, which formats the data into any one of a number of telemetry frame formats used in the pacemaker industry. The processor 108 transfers the telemetry frame to a modulator 110, which modulates the telemetry frame on to a carrier. The modulator 110 transfers the modulated signal to a transmit coil driver 112, which transmits the modulated data to the programmer 102 over the pacemaker coil 104.

Through the programmer coil 106, the modulated telemetry frame is received by a programmer receiver 114, which forwards the signal to a demodulator 116. The demodulator 116 recovers the baseband telemetry frame signal from the modulated signal. In normal operation, the demodulated signal is passed through a decision logic circuit 118, which provides a bit pattern of ones and zeros in response to the analog baseband signal received from the demodulator 116.

The binary data is forwarded to a programmer processor 120 for processing. The programmer processor 120 may, for example, interpret battery condition measurements sent by the pacemaker 100 and determine that the battery end-of-life condition has been reached, and therefore the pacemaker must be replaced. Alternatively, an analysis of ECG data received from the pacemaker may reveal that the heart is beating too slowly. In that case, a physician operating the programmer 102 may input a command into an input/output device 121, such as a keyboard, to instruct the processor 120 to issue a command to the pacemaker 100 to increase the pacing rate. This command signal will be modulated by a programmer modulator 122 and transmitted back to the pacemaker 100 through a programmer transmit coil driver 124 and over the programmer coil 106. A pacemaker receiver 126 receives the command through the coil 104 and forwards the modulated signal to a demodulator 128, which recovers the baseband command signal. The demodulated baseband command signal is digitized through a decision logic circuit 130. The pacemaker processor 108 implements the actions specified by the command signal, such as instructing the pacemaker 100 to increase the pacing rate.

As discussed above, conventional telemetry systems operate at a fixed pacemaker transmitter power level. The present invention provides an improvement over the prior art by allowing the radiated transmitter power to be adjusted so as to guarantee satisfactory telemetry, while minimizing pacemaker power consumption. The operation of the present invention will now be described with reference to the block diagram of FIG. 1 and the flow chart of FIG. 2.

Figure 2:
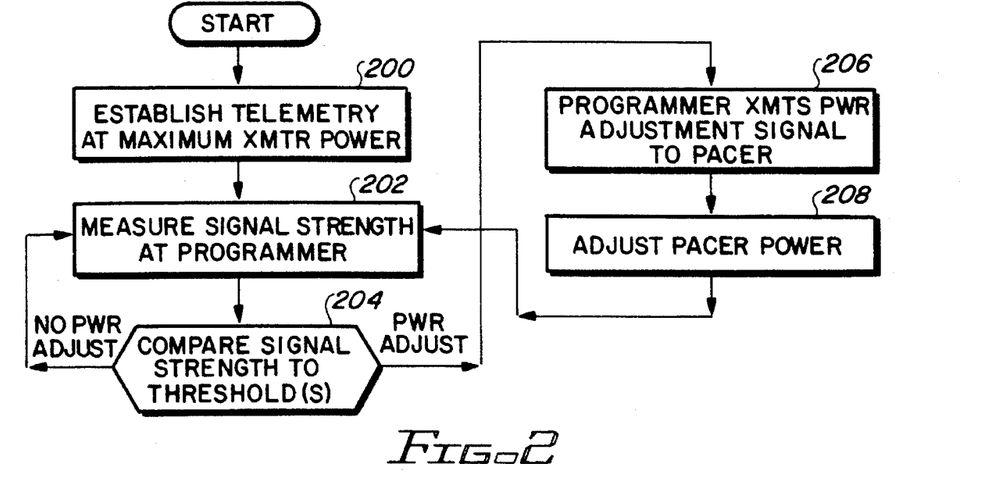
FIG. 2 is a flowchart diagramming the process generally used by the present invention.

The power setting process starts with the establishment of telemetry between the programmer 102 and the pacemaker 100 using a standard handshake protocol known in the art. Initially, the transmitter power is set to a maximum level by the pacemaker processor 108 (step 200). The pacemaker processor 108 transfers a command that is denoted the power control word (PCW) to a power control circuit 132 in order to adjust the power output of the transmit control driver 112. The power control circuit 132 may be implemented using active or passive techniques well known in the art. Further, in one embodiment the power control word may be a three bit word whereby the binary string 000 represents the maximum power setting of the pacemaker transmit coil driver 112. Higher values of the PCW represent lower power settings with PCW =111 (binary) =7 (base 10) representing the minimum power setting.

The maximum power telemetry signal transmitted by the pacer 100 is received through inductive coupling by the programmer receiver 114. For power setting purposes, the received signal is demodulated by the demodulator 116 and forwarded to an analog-to-digital converter (ADC) 134. The ADC 134 digitizes the amplitude of the received telemetry signal, thus providing a measure of the strength of the telemetry signal (step 202). Other measures of signal strength, such as the signal-to-noise ratio, may also be provided at this point using additional circuitry known in the art.

The received signal strength is compared to one or more predetermined thresholds by a comparator 136 to determine whether the signal strength is at a satisfactory level (step 204). If so, then the telemetry system continues the monitoring of signal strength (step 202). If not, then the comparator 136 issues a signal to the processor 120 indicating that pacemaker transmitter power must be adjusted. The signal issued by the comparator 136 may indicate that an increase in power is necessary by issuing a 1 bit, while a signal to decrease power may be represented by a 0 bit.

Based upon the determination made by the comparator 136, the processor 120 generates a command to the pacer 100 to control the pacer transmitter power (step 206). This command is transmitted to the pacemaker 100 and used by the pacemaker processor 108 and the power control circuit 132 to adjust the pacer transmitter power (step 208). The programmer 102 continues to monitor the signal strength of the telemetry signal and adjusts the power accordingly to maintain effective telemetry as dictated by the threshold(s) used by the comparator 136.

Figure 3:
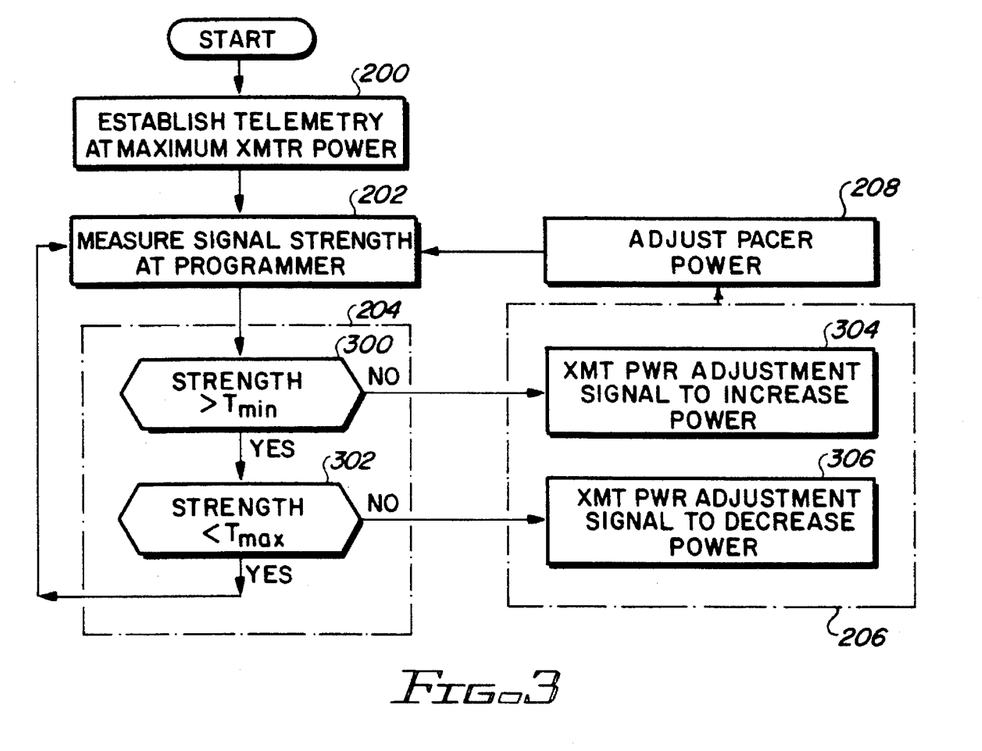
FIG. 3 is a flowchart of the dual threshold embodiment of the present invention.

FIG. 3 illustrates an embodiment of the present invention in which the comparator 136 uses two thresholds: a minimum signal strength threshold $T_{min}$, which represents the minimum received signal strength required to maintain effective telemetry; and a maximum threshold $T_{max}$, which indicates that the signal strength is more than adequate and that any increase above $T_{max}$ would result in an unacceptable drain on the pacemaker battery. The comparator 136 determines whether the received signal strength is greater than $T_{min}$ and less than $T_{max}$ (steps 300 and 302). If the signal strength is within those bounds, then the pacemaker transmitter power need not be adjusted because the signal strength is adequate to provide satisfactory telemetry without causing unnecessary power consumption. However, if the measured signal strength does not exceed $T_{min}$ (step 300), the comparator 136 issues a signal to the programmer processor 120 indicating that pacemaker transmitter power must be increased to maintain effective telemetry. In response, the programmer processor 120 issues a command to the pacer 100 to increase transmitter power (step 304). On the other hand, if the measured signal strength is greater than or equal to $T_{max}$ (step 302), then the comparator 136 issues a signal to the processor 120 indicating that pacemaker transmitter power must be decreased to avoid unnecessary current drain on the pacemaker battery. In response to this signal, the processor 120 instructs the pacer 100 to decrease power (step 306). The pacemaker 100 adjusts its power accordingly (step 208), and the process continues so as to maintain effective telemetry while preventing unacceptable drain on the pacer battery.

The generalized power setting method of the present invention shown in FIG. 2 may also be implemented using only $T_{min}$. Two single-threshold power setting algorithms —the sequential method and the binary search method —will be described herein, but the present invention should be understood not to be limited to these techniques.

Figure 4:
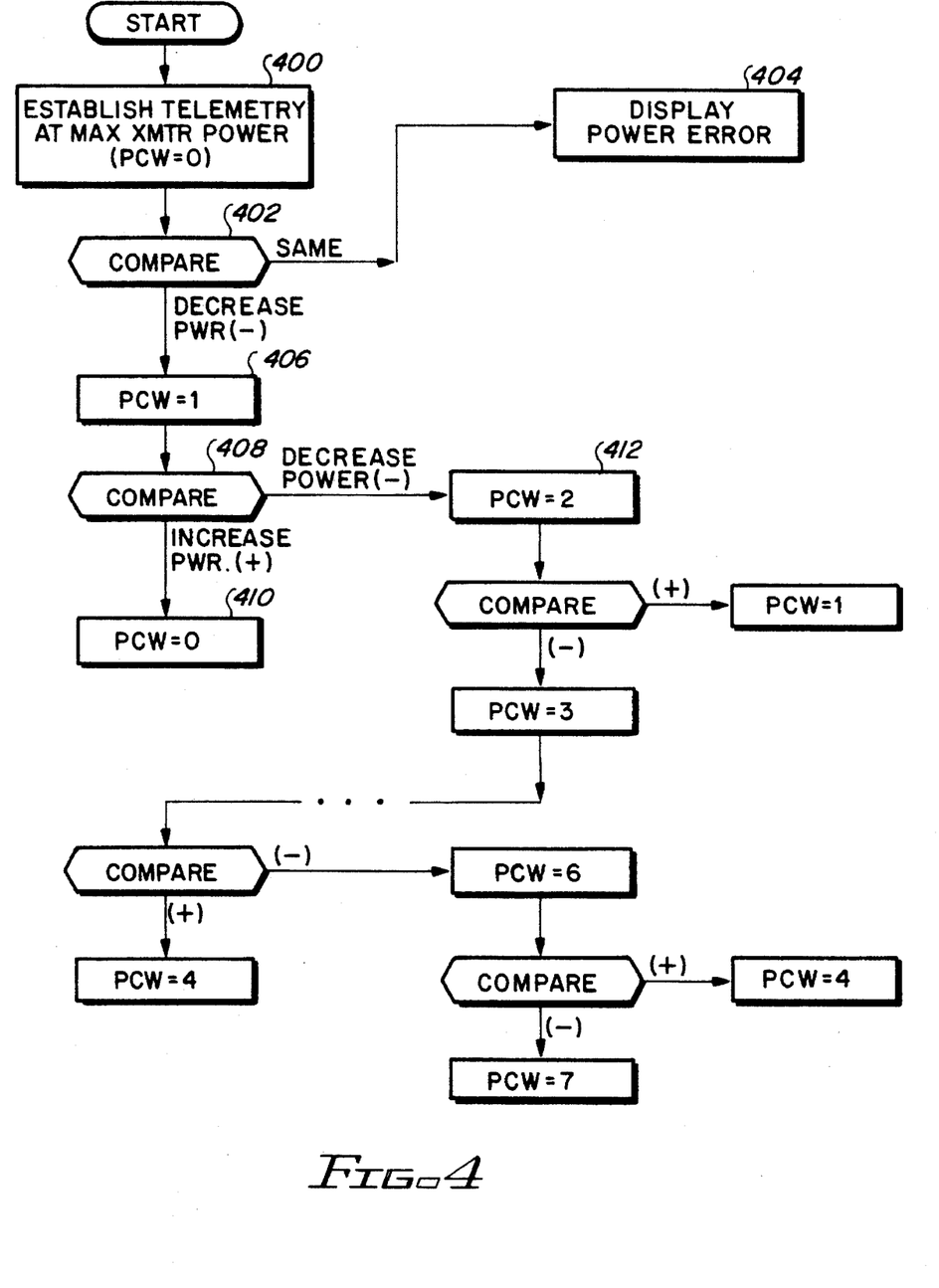
FIG. 4 is a flowchart of the sequential power setting technique used by the present invention.

FIG. 4 illustrates the single-threshold power setting procedure using the sequential method. With this technique, power is increased or decreased in fixed increments according to the determination made by the comparator 136. As before, telemetry is established at maximum transmitter power (step 400). At maximum transmitter power, the PCW equals 0. The programmer 102 then measures the signal strength of the received signal, and compares the signal strength to $T_{min}$ (step 402). (The step of measuring the signal strength is not shown to avoid complicating the flowchart.) If the received signal strength falls below the threshold at maximum transmitter power then the pacemaker power cannot be adjusted to obtain satisfactory telemetry. In that event, the programmer 102 displays a "power error" indication on the input/output device 121 (step 404).

If however, the received signal strength lies above $T_{min}$, then the programmer 102 transmits a power adjustment signal to the pacer instructing it to decrease its power. Using the sequential method, the power is decreased here by a fixed amount as represented by the incrementation of the PCW to a value of 1 (step 406). (The step of transmitting the power adjustment signal to the pacer has been omitted to avoid unnecessarily complicating the flow chart.) The signal strength of the new received telemetry signal is then measured (step not shown), and compared to $T_{min}$ (step 408). If the signal strength at the new setting is determined to be too low, then the power is incremented back to its maximum value (PCW =0) and the power setting sequence is temporarily halted (step 410). If, however, the comparator 136 determines that the power may be decreased further, than the power is decreased by incrementing the PCW to a value of 2 (step 412), and the process continues as shown in FIG. 4.

The power setting sequence will eventually end when either of two conditions is satisfied. First, the process will stop if the comparison requires that the power be increased back to a previous setting (e.g., step 410). Alternatively, the power will be continually decreased until it reaches a minimum power setting represented by PCW =7 for a three bit PCW. To allow for changes in the signal environment during telemetry, this power setting sequence may be restarted periodically as desired.

Figure 5:
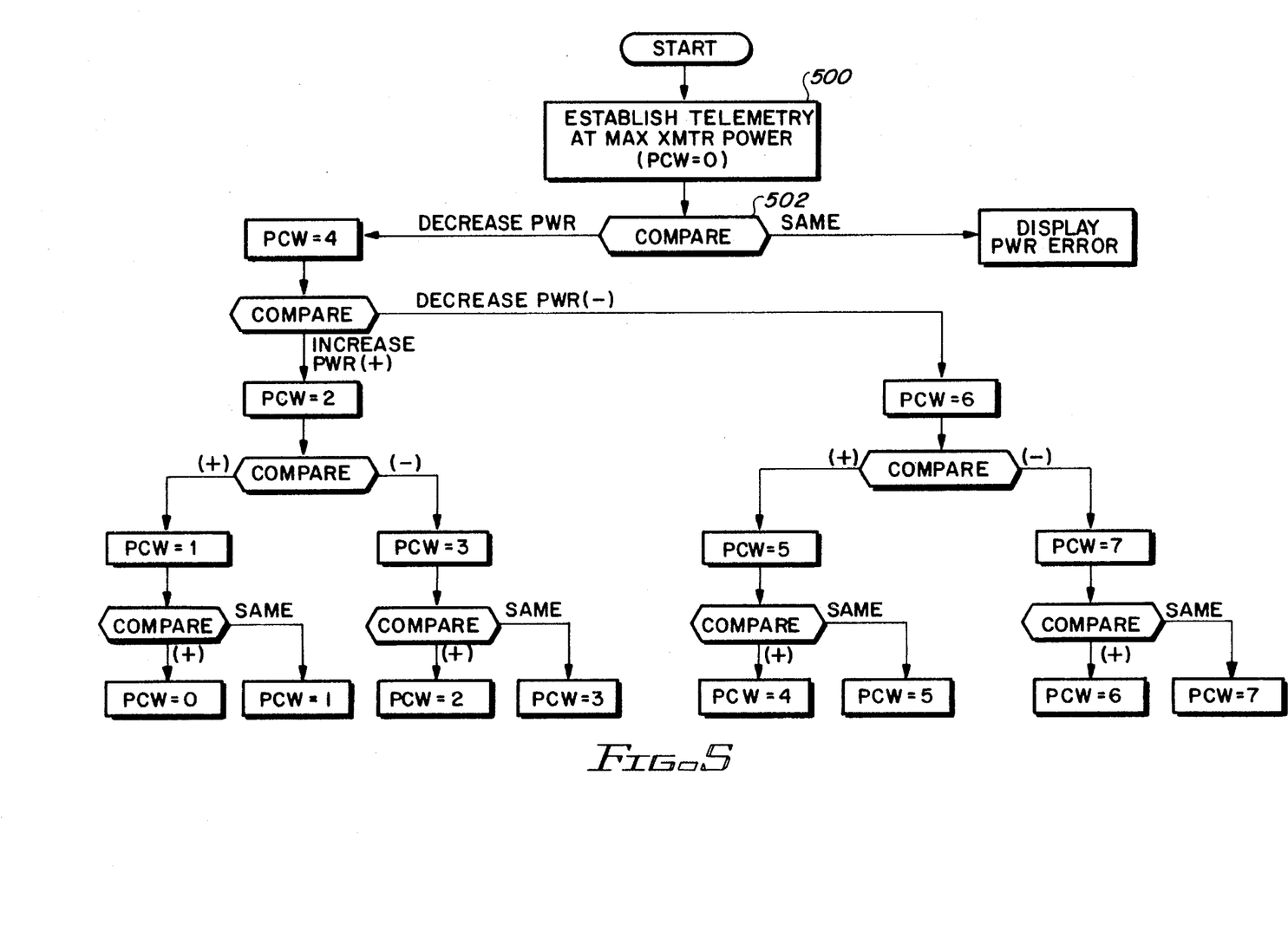
FIG. 5 is a flowchart of the binary decision tree used by the present invention for power setting.

Power setting using a binary search tree is illustrated in FIG. 5. As before, telemetry is established at maximum transmitter power (step 500). The programmer 102 measures the received signal strength (step not shown), and compares the signal strength to $T_{min}$ (step 502). Based upon the determination made by the comparator 136, the processor 120 then determines the optimum power setting according to the binary decision tree of power control words illustrated in FIG. 5.

A comparison of the decision trees for the sequential and binary search modes reveals that the sequential method requires a longer settling time. However, because the sequential process adjusts the power in smaller increments than the binary search technique, the pacemaker is less likely to lose telemetry in the sequential mode when power is adjusted downward. If telemetry is lost, then the system must reestablish communication. Because the binary method is more likely to decrease power in larger increments, the binary search method could in practice take more time than the sequential technique.

The power adjustment signal transmitted by the programmer 102 may take on two different forms. In the "smart programmer" mode, the programmer processor 120 generates the power control word and transmits it to the pacer 100, which uses it directly to control the power control circuit 132. In this mode, the programmer processor 120 executes the algorithm used to calculate the power control word. For example, the programmer processor 120 could execute the software implementing the binary search tree of FIG. 5.

Alternatively, in the "smart pacemaker" mode, the pacemaker, not the programmer, determines the power control word. After measuring the received signal strength and performing the comparison process, the programmer 102 transmits not the power control word, but rather only the comparator signal to the pacer 100. This comparator signal indicates only whether power is to be increased or decreased and not the actual value of the power control word. The pacer processor 108 uses this comparator signal to calculate the power control word using one of the algorithms described above. Thus, the software implementing those algorithms must be executed inside the pacer 100 by the pacer processor 108.

Figure 6:
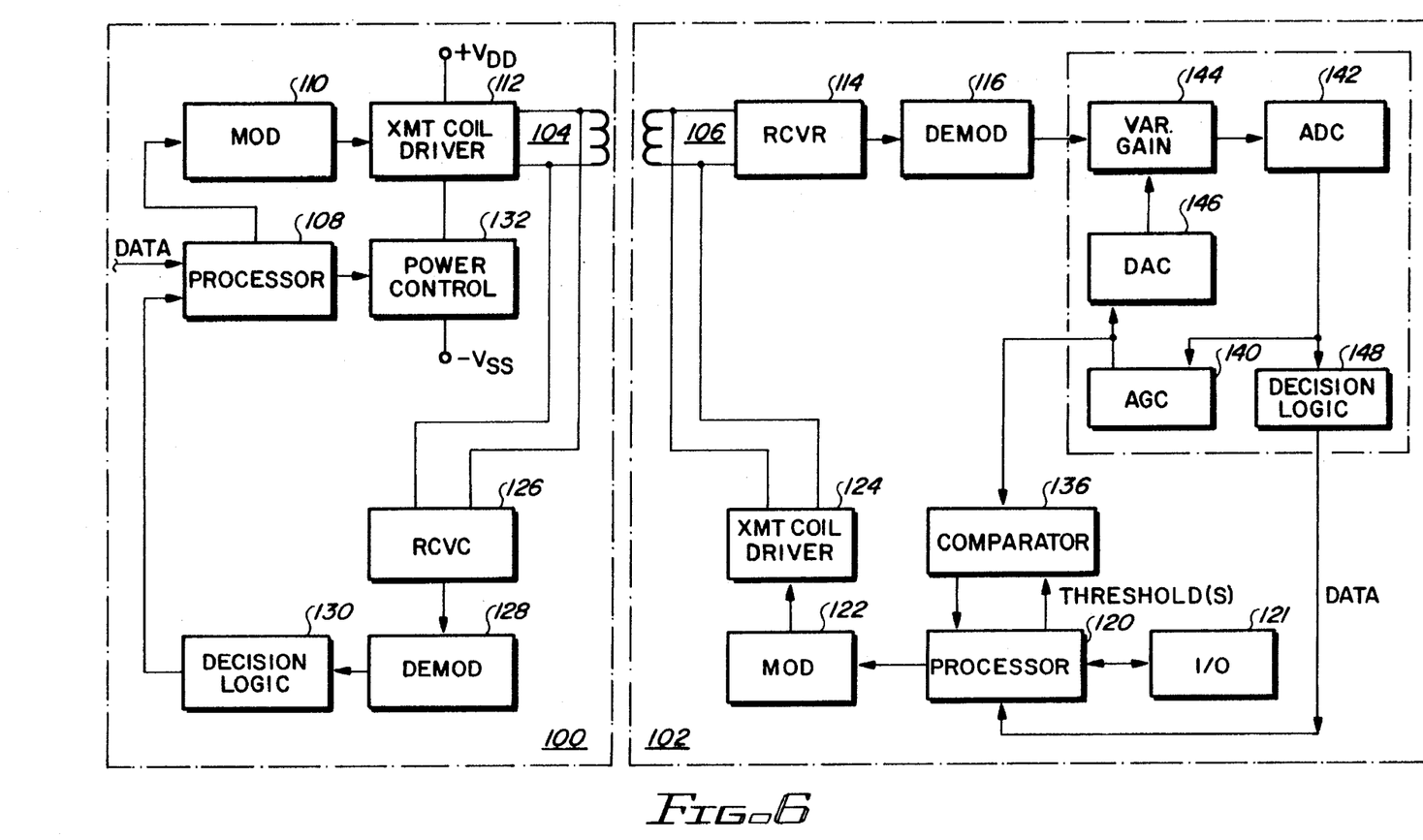
FIG. 6 illustrates an alternate embodiment of the telemetry system of the present invention that incorporates an automatic gain control.

Another embodiment of the present invention is shown in FIG. 6. This implementation takes advantage of the gain indicator provided by an automatic gain control (AGC) 140 that is incorporated into the programmer 102. The AGC 140 ensures that the demodulated waveform presented to an analog-to-digital converter (ADC) 142 utilizes the full input range of the ADC 142. The signal transmitted by the pacer 100 is received and demodulated by the programmer 102 and fed into a variable gain amplifier 144. The output of the amplifier is fed into the ADC 142, which digitizes the amplitude of the received signal. Based upon this amplitude, the AGC 140 determines whether the full range of the ADC 142 is being utilized. If not, the AGC 140 increases the gain if it receives a low amplitude signal representation, and conversely decreases the gain if it appears that the signal level is too high. This new gain, which is in digital form, is passed through a digital-to-analog converter (DAC) 146 to convert it to an analog gain control used by the variable gain amplifier 144. After the AGC 140 has passed through a few iterations of this adjustment process, the gain settles to a value ensuring that the demodulated signal uses the full range of the ADC 142. The telemetry system may then commence normal operation, wherein the decision logic 148 determines whether the ADC 142 output representing the demodulated pacemaker signal is a binary 0 or a binary 1.

The embodiment of the present invention incorporating the AGC operates in essentially the same manner as the previous embodiment except for the treatment of the threshold in the comparator 136. The gain level provided by the AGC 140 is fed in digital form to the comparator 136. A high gain indicates that the received signal strength is weak, while a low gain represents a strong signal. Because the AGC gain is inversely proportional to the signal strength, the roles of the thresholds in this embodiment are the reverse of those in the previous embodiments. Let $T_{Gmax}$, represent a maximum gain threshold. If G is defined as the gain from the AGC 140 and $G > T_{Gmax}$, then transmitter power should be increased because the high gain represents a weak signal. Also, let $T_{Gmin}$, represent a minimum gain threshold, below which point the gain represents a strong signal resulting in unnecessary pacer power consumption. If $G < T_{Gmin}$, then transmitter power should be decreased. Thus, the comparator signal is determined in this manner. In all other respects, the operation of this embodiment is essentially the same as that of the previous embodiments.

The present invention may use a number of techniques to determine $T_{min}$ or $T_{Gmax}$, the minimum signal strength threshold necessary to maintain satisfactory telemetry. In general, the minimum threshold may be set using static or dynamic methods. Using the static technique, the threshold is determined under laboratory conditions during the design of the pacemaker. A worst case scenario requiring maximum pacemaker transmitter power may be set up by using a maximum telemetry distance of approximately four inches in a noisy electrical environment. The pacemaker is programmed to transmit a known binary sequence. The bit error rate is then measured at the programmer. Using well known signal processing techniques, the threshold is determined to be the minimum transmitter power (or maximum AGC gain) necessary to guarantee an acceptable error rate.

The minimum signal strength threshold may also be determined dynamically to adapt to the environment in which telemetry is actually being conducted. In most situations, the worst case is not realized, and thus the threshold may be adjusted to reduce pacemaker current drain and increase battery life.

Dynamic threshold setting may be carried out while the pacemaker is implanted, and not just in the laboratory environment. In threshold setting mode, the programmer processor 120 instructs the pacemaker to transmit a binary string of zeros. The received signal strength (or AGC gain) is measured at the input to the comparator 136. A signal strength above the level measured for the zero input (or gain below that level) must represent the presence of a binary one. Thus, the signal strength (or AGC gain) measured with the zero input represents a nominal threshold level. To guarantee discrimination between zero and one bits, however, a small safety margin is added to the nominal threshold (or subtracted for the AGC embodiment) to produce the actual threshold used by the comparator. This safety margin may be determined in the laboratory using well known estimation techniques.

The maximum signal quality ($T_{max}$ or $T_{Gmin}$) may be determined in the laboratory by increasing transmitter power until a predetermined current drain on the pacer battery is measured. Empirical evidence has shown that an unacceptable current drain occurs when the battery current is approximately two to three times that measured at the minimum signal quality threshold.

Although the invention has been described in conjunction with preferred embodiments, it will be appreciated that various modifications and alterations may be made by those skilled in the art without departing from the spirit and scope of the invention. In particular, the present invention may determine transmitter power level using other measures of signal quality, such as bit error rate, as well as the measures described herein.

What is claimed is:

1. In a system comprising an implantable medical device and an external programmer, the implantable medical device having a transmitter for transmitting telemetry signals between the implantable medical device and the external programmer and a receiver for receiving telemetry signals transmitted from the external programmer, the transmitter having a power level, the implantable medical device including means for adjusting the transmitter power level, the telemetry signals having a signal strength, the programmer including means for receiving and transmitting telemetry signals between the programmer and the implantable medical device, means for generating a power control signal, and means for determining the strength of the telemetry signals received by the programmer, a method of controlling the transmitter power of the implantable medical device comprising the steps of:

(a) measuring the strength of the telemetry signals received by the programmer;

(b) generating a power control signal, by the programmer, as a function of the measured signal strength;

(c) transmitting the power control signal to the implantable medical device; and (d) adjusting the transmitter power of the implantable medical device to a power level as a function of the power control signal.

2. The method of claim 1, further comprising the step of:

(e) repeating steps (a), (b), (c), and (d) until the measured signal strength satisfies a predetermined signal strength condition.

3. The method of claim 1, wherein step (b) comprises the steps of:

comparing the measured signal strength to at least one threshold value to thereby provide a comparator signal, the comparator signal indicating whether the power level is to be increased or decreased; and generating the power control signal as a function of the comparator signal.

4. The method of claim 3, wherein:

a first threshold ($T_{min}$) represents a minimum acceptable signal strength;

a second threshold ($T_{max}$) represents a maximum acceptable signal strength, the method further comprising the steps of:

comparing the measured signal strength to $T_{max}$ and to $T_{min}$;

providing a power control signal to increase the power level if the measured signal strength is less than the $T_{min}$; and providing a power control signal to decrease the power level if the measured signal strength is greater than the $T_{max}$.

5. The method of claim 3, wherein:

the external programmer includes automatic gain control (AGC) means for amplifying the received telemetry signals at gain levels for providing an output signal thereof at a constant value, the gain level being inversely proportional to the measured signal strength, a first threshold represents a maximum acceptable gain level, a second threshold represents a minimum acceptable gain leve, wherein the generating step further comprises:

generating the power control signal, the power control signal indicating that the power level is to be increased if the gain level is greater than the first threshold; and the power control signal indicating that the power level is to be decreased if the gain level is less than the second threshold.

6. The method of claim 3, further comprising the step of:

establishing telemetry at a maximum transmitter power level before step (a).

7. The method of claim 6, the method further comprising the steps of:

(e) repeating steps (a), (b), (c), and (d) until the comparator signal, in step (b), indicates that the power level is to be increased, then performing steps (c) and (d) and halting thereafter.

8. The method of claim 6, wherein the power level is set by the power control signal according to a binary decision tree of power level settings, wherein:

the power level has a step size indicating the smallest amount by which the power level may be increased or decreased; and the establishing step further comprises establishing a power adjustment value equivalent to half the maximum transmitter power level;

step (b) further comprises generating the power control signal by adding the power adjustment value if the comparator signal indicates that the power level is to be increased or subtracting the power adjustment value if the comparator signal indicates that the power level is to be decreased; and the method further comprises the steps of:

(e) setting the power adjustment value to half of the previous value of the power adjustment value;

(f) repeating steps (a), (b), (c), (d), and (e) until the power adjustment value is less than the power level step size.

9. The method of claim 6, wherein:

the power control signal indicates that the power level is to be adjusted by incrementing or decrementing the power level by a predetermined amount in response to the comparator signal, the at least one threshold is a first threshold representing a minimum acceptable signal strength ($T_{min}$); and the method further comprises the steps of:
  (e) adjusting the power control signal for decrementing the power level by the predetermined amount;
  (f) repeating steps (a), (b), (c), (d), and (e) if the measured signal strength is greater than ($T_{min}$); and
  (g) adjusting the power control signal for incrementing the power level by the predetermined amount if the measured signal strength is less than ($T_{min}$) and halting thereafter.

10. The method of claim 9, further comprising the step of:
  (h) providing an alarm signal if the measured signal strength fails to exceed ($T_{min}$).

11. The method of claim 9, wherein the at least one threshold comprises a first threshold representing a minimum acceptable signal strength and a second threshold representing a maximum signal strength, the first and second thresholds defining an acceptable signal strength band therebetween, the method further comprising the steps of:

adjusting the power control signal for decrementing the power level by the predetermined amount;

comparing the measured signal strength to the acceptable signal strength band; and repeating steps (f) and (g) until the measured signal strength falls within the acceptable signal strength band.

12. The method of claim 3, further comprising the steps of:

transmitting a threshold setting signal from the implantable device to the programmer, wherein the threshold setting signal represents at least one binary zero and the at least one threshold includes a first threshold representing a minimum acceptable signal strength;

measuring the signal strength of the threshold setting signal at the programmer, thereby generating a signal strength measurement; and setting the first threshold to the signal strength measurement plus a safety margin.

13. An implantable medical device for use with and in telemetry communication with an external programmer, the implantable medical device transmitting telemetry signals, the telemetry signals having a signal strength, and the external programmer transmitting a power control signal to the implantable medical device as a function of the signal strength, the implantable medical device comprising:

a biocompatible housing containing circuitry generating implantable device signals suitable for implanting in body tissue;

transmitter means for transmitting telemetry signals corresponding to implantable medical device signals at a power level;

receiver means for receiving a power control signal from the external programmer; and processing means for adjusting the power level of the transmitter means in response to the power control signal, wherein the power control signal is a function of the signal strength of the telemetry signals received by the programmer, wherein the transmitter means, the receiver means and the processing means are housed within the biocompatible housing.

14. The implantable medical device of claim 13 further comprising:

means for defining a first threshold representing a minimum acceptable signal strength;

means for defining a second threshold representing a maximum acceptable signal strength; and wherein the processing means adjusts the power level by increasing the power level if the power control signal is less than the first threshold or decreasing the power level if the power control signal is greater than the second threshold.

15. An external programmer for use and in telemetry communication with an implantable medical device, the implantable medical device having a first transmitter means for transmitting telemetry signals having a signal strength at adjustable power levels and a first receiver means for receiving command signals, wherein the implantable medical device has a first processing means that varies the power level of the first transmitter as a function of the received command signal, the programmer for controlling the transmitter power level of the implantable medical device, the programmer comprising:

second receiver means for receiving telemetry signals from the implantable medical device;

means for measuring the signal strength of the received telemetry signals;

second processing means for generating a command signal as a function of the signal strength of the telemetry signals received from the implantable device; and second transmitter means for transmitting the command signal to the implantable device.

16. The programmer of claim 15 further comprising:

means for defining a first threshold representing a minimum acceptable signal strength;

means for defining a second threshold representing a maximum acceptable signal strength; and wherein the second processing means includes means for adjusting the command signal to indicate that the power level is to be increased if the signal strength is less than the first threshold and to indicate that the power level is to be decreased if the signal strength is greater than the second threshold.

17. The programmer of claim 15, further comprising:

automatic gain control means for amplifying the received telemetry signals at gain levels for providing an output signal thereof at a constant value, wherein the gain level is inversely proportional to the signal strength;

means for defining a first threshold representing a maximum acceptable gain level;

means for defining a second threshold representing a minimum acceptable gain level; and wherein the second processing means includes means for adjusting the command signal to indicate that the power level is to be increased if the gain level is greater than the first threshold and to indicate that the power level is to be decreased if the gain level is less than the second threshold.

18. The programmer of claim 15 further comprising:

comparator means for comparing the signal strength of the received telemetry signals to at least one threshold to thereby provide a comparator signal, the second processing means further for generating the command signal as a function of the comparator signal, the comparator signal indicating whether the power level is to be increased or decreased, the command signal specifying the power level of the first transmitter.

19. The programmer of claim 15 further comprising:

comparator means for comparing the signal strength of the received telemetry signals to at least one threshold to thereby provide a comparator signal, the comparator signal indicating whether the power level is to be increased or decreased, the second transmitter means transmitting the comparator signal as the command signal.

20. A system for controlling a power level of telemetry signals between an implantable medical device and an external programmer, the system comprising an implantable medical device and an external programmer, the implantable medical device comprising:

first transmitter means for transmitting telemetry signals having controllable power level;

first receiver means for receiving command signals from the external programmer; and processor means for controlling the power level of the first transmitter means as a function of the command signals, said telemetry signals having a signal strength; and the external programmer comprising:
second receiver means for receiving telemetry signals from the implantable medical device, wherein the telemetry signals have a signal strength;
means for generating the command signals as a function of the received telemetry signals; and
second transmitter means for transmitting the command signals to the implantable medical device, the command signals indicating that the first transmitter means power level is to be increased or decreased as a function of the signal strength.

21. The system of claim 20, wherein the external programmer further comprises:

comparator means for comparing the signal strength to at least one threshold, thereby generating a comparator signal; and means for generating the command signals as a function of the comparator signal.

22. The system of claim 21, wherein the at least one threshold comprises first and second thresholds and wherein the generating means further comprises means for providing command signals that indicate that the first transmitter means power level is to be increased if the signal strength is less than the first threshold and for indicating that the first transmitter means power level is to be decreased if the signal strength is greater than the second threshold.

23. The system of claim 20, wherein the implantable medical device further comprises:

means for transmitting a threshold setting signal, having a signal strength, the threshold setting signal representing at least one binary zero; and the external programmer further comprises:
means for receiving the threshold setting signal;
means for measuring the signal strength of the received threshold setting signal, thereby generating a signal strength measurement; and
means for generating a threshold as a function of the signal strength measurement and a safety margin; and wherein the means for generating the command signals generates the command signals as a function of the threshold.

24. The system of claim 20, wherein the external programmer further comprises:

automatic gain control means for amplifying the received telemetry signals at gain levels for providing an output signal thereof at a constant value, wherein the gain level is inversely proportional to the signal strength of the telemetry signals; and wherein the means for generating the command signals generates the commands signals as a function of the gain level.

25. The system of claim 24, wherein the means for generating the commands signals generates the commands signals by comparing the gain level to a first threshold representing a maximum acceptable gain level, generating command signals that indicate the power level of the first transmitter is to be increased if the gain level is greater than the first threshold, by comparing the gain level to a second threshold representing a minimum acceptable gain level, and generating command signals that indicate the power level of the first transmitter is to be decreased if the gain level is less than the second threshold.

26. In a system comprising an implantable medical device and an external programmer, the implantable medical device having a transmitter for transmitting telemetry signals between the implantable medical device and the external programmer, the transmitter having a controllable power level, the implantable medical device further having a receiver for receiving telemetry signals transmitted from the external programmer, the implantable medical device including means for generating a power control signal and means for adjusting the transmitter power level, the telemetry signals having a signal strength, the programmer including means for receiving and transmitting telemetry signals between the programmer and the implantable medical device and means for determining the strength of the telemetry signals received by the programmer, a method of controlling the transmitter power level of the transmitter of the implantable medical device comprising the steps of:

(a) measuring the strength of the telemetry signals received by the programmer, thereby creating a strength measurement signal;

(b) transmitting the strength measurement signal to the implantable medical device (c) generating a power control signal, by the implantable medical device, as a function of the received strength measurement signal; and (d) adjusting the transmitter power level of the transmitter of the implantable medical device as a function of the power control signal.

27. The method of claim 26, further comprising the step of:

(e) repeating steps (a), (b), (c), and (d) until the measured signal strength satisfies a predetermined signal strength condition.

28. The method of claim 26, wherein step (a) comprises the steps of:

comparing the measured signal strength to at least one threshold value to thereby provide a comparator signal, the comparator signal indicating whether the power level is to be increased or decreased; and generating the power strength measurement signal as a function of the comparator signal.

29. The method of claim 28, wherein:

a first threshold ($T_{min}$) represents a minimum acceptable signal strength;

a second threshold ($T_{max}$) represents a maximum acceptable signal strength, the method further comprising the steps of:

comparing the measured signal strength to $T_{max}$ and to $T_{min}$;

providing a strength measurement signal that indicates the power level is to be increased if the measured signal strength is less than the $T_{min}$; and providing a strength measurement signal that indicates the power level is to be decreased if the measured signal strength is greater than the $T_{max}$.

30. The method of claim 28, further comprising the step of:

establishing telemetry at a maximum power level before step (a).

31. The method of claim 30, the method further comprising the steps of:

(e) repeating steps (a), (b), (c), and (d) until the comparator signal, in step (a), indicates that the power level is to be increased, then performing steps (b), (c), and (d) and halting thereafter.

32. The method of claim 30, wherein the power level is set by the power control signal according to a binary decision tree of power level settings, wherein:

the power level has a step size indicating the smallest amount by which the power level may be increased or decreased; and the establishing step further comprises establishing a power adjustment value equivalent to half the maximum transmitter power level;

step (c) further comprises generating the power control signal by adding the power adjustment value if the comparator signal indicates that the power level is to be increased or subtracting the power adjustment value if the comparator signal indicates that the power level is to be decreased; and the method further comprises the steps of:

(e) setting the power adjustment value to half of the previous value of the power adjustment value;

(f) repeating steps (a), (b), (c), (d), and (e) until the power adjustment value is less than the power level step size.

33. The method of claim 28, further comprising the steps of:

transmitting a threshold setting signal from the implantable device to the programmer, wherein the threshold setting signal represents at least one binary zero and the at least one threshold includes a first threshold representing a minimum acceptable signal strength;

measuring the signal strength of the threshold setting signal at the programmer, thereby generating a signal strength measurement; and setting the first threshold to the signal strength measurement plus a safety margin.

* * * * *